United States Patent
Maitre et al.

(10) Patent No.: US 12,265,084 B2
(45) Date of Patent: Apr. 1, 2025

(54) METHOD FOR ANALYZING THE PLATELETS OF A BLOOD SAMPLE

(71) Applicants: ETABLISSEMENT FRANCAIS DU SANG, Saint-Denis (FR); INSTITUT NATIONAL DE LA SANTE ET DE LA RECHERCHE MEDICALE (INSERM), Paris (FR); UNIVERSITE DE STRASBOURG, Strasbourg (FR)

(72) Inventors: Blandine Maitre, Strasbourg (FR); Catherine Angenieux, Strasbourg (FR); Henri De La Salle, Strasbourg (FR); Christian Gachet, Lalaye (FR)

(73) Assignees: ETABLISSEMENT FRANCAIS DU SANG, Saint-Denis (FR); INSTITUT NATIONAL DE LA SANTE ET DE LA RECHERCHE MEDICALE (INSERM), Paris (FR); UNIVERSITE DE STRASBOURG, Strasbourg (FR)

( * ) Notice: Subject to any disclaimer, the term of this patent is extended or adjusted under 35 U.S.C. 154(b) by 1103 days.

(21) Appl. No.: 17/263,269

(22) PCT Filed: Jul. 29, 2019

(86) PCT No.: PCT/FR2019/051867
§ 371 (c)(1),
(2) Date: Jan. 26, 2021

(87) PCT Pub. No.: WO2020/025891
PCT Pub. Date: Feb. 6, 2020

(65) Prior Publication Data
US 2021/0148919 A1    May 20, 2021

(30) Foreign Application Priority Data

Jul. 30, 2018 (FR) ..................................... 1857095

(51) Int. Cl.
*G01N 33/58* (2006.01)
*G01N 33/49* (2006.01)

(52) U.S. Cl.
CPC ....... *G01N 33/582* (2013.01); *G01N 33/4915* (2013.01); *G01N 2800/222* (2013.01); *G01N 2800/32* (2013.01); *G01N 2800/50* (2013.01); *G01N 2800/52* (2013.01)

(58) Field of Classification Search
CPC ............. G01N 33/582; G01N 33/4915; G01N 2800/222; G01N 2800/32; G01N 2800/50; G01N 2800/52
See application file for complete search history.

(56) References Cited

FOREIGN PATENT DOCUMENTS

WO    2009058876 A1    5/2009

OTHER PUBLICATIONS

Vucetic et al., Blood Transfus 2018: 16: 83-92 (Year: 2018).*
French Search Report issued in corresponding French Application No. 1857095 on Apr. 26, 2019, 1 page.
International Search Report issued in corresponding International Application No. PCT/FR2019/051867 on Dec. 13, 2019, 3 pages.
Abcam. "Product datasheet Anti-HLA Class I antibody [W6/32]" Apr. 12, 2006, http://www.abcam.com/hla-class-i-anitbody-w632-ab22432.html XP055583711.
Binta Shah et al., "Mean platelet volume reporducibility and association with platlet activity and anti-platelet therapy", Platelets (London), GB, vol. 25, No. 3, 2014, pp. 188-192, DOI: 10.3109/09537104.2013.793794 ISSN: 0953-7104, XP 055583721.
Chapman Lesley M. et al., "Platelets Present Antigen in the Context of MHC Class I." The Journal of Immunology, Jun. 15, 2012, vol. 189, No. 2, 916-923, pp. 1-17, PubMed Central (PMC) Author Manuscript, http://www.ncbi.nlm.nih.gov/pmc/articles/PMC3392496/ XP055583680.
Angènieux, Catherine, "Cell surface expression of HLA I molecules as a marker of young platelets", Journal of Thrombosis and Haemostasis, Wiley Online Library, Jun. 17, 2019, vol. 17, No. 9, http://onlinelibrary.wiley.com/doi/epdf/10.1111/jth.14537 XP055647140.
Vučetić et al., Flow cytometry analysis of platelet populations: usefulness for monitoring the storage lesion in pooled buffy-coat platelet concentrates, Blood Transfus, Jan. 2018, vol. 16, No. 1, pp. 83-92.

* cited by examiner

*Primary Examiner* — Robert S Cabral
(74) *Attorney, Agent, or Firm* — MH2 Technology Law Group, LLP

(57) ABSTRACT

The present invention relates to a method for analyzing the platelets present in a blood sample, said method comprises the steps of (a) adding to said sample a ligand which binds to the MCH I coupled to a fluorochrome, (b) measuring the mean fluorescence intensity of the platelets ($MFI_{platelets}$) with a flow cytometer and c) measuring the mean "Forward Scatter" parameter (FSC) with said flow cytometer and determining the $MFI_{platelets}/FSC$ ratio. The invention also relates to an in vitro method for diagnosing a peripheral or central thrombocytopenia in a subject.

20 Claims, 7 Drawing Sheets

D

METHOD FOR ANALYZING THE PLATELETS OF A BLOOD SAMPLE

CROSS REFERENCE TO RELATED APPLICATIONS

This application is the National Phase of PCT International Application No. PCT/FR2019/051867, filed on Jul. 29, 2019, which claims priority under 35 U.S.C. 119(a) to Patent Application No. 1857095, filed in France on Jul. 30, 2018, all of which are hereby expressly incorporated by reference into the present application.

FIELD OF THE INVENTION

The present invention relates to the field of in vitro blood analysis processes and in particular the field of processes for analyzing platelets present in a blood sample. More particularly, the process according to the invention can be used to diagnose in vitro peripheral or central thrombocytopenia in a subject.

TECHNICAL BACKGROUND

Platelets are blood cells which lack a nucleus and are produced by fragmentation of the megakaryocytes in the bone marrow. They are normally present in the blood at an average concentration of 150 000 to 400 000 /µL in humans and have an essential role in hemostasis, a biological process encompassing all the phenomena that prevent and stop bleeding.

A number of pathologies are related to abnormalities in the number of platelets in the blood. These may be an increase in the concentration of platelets in the blood, i.e., thrombocytosis, or a decrease in the concentration of platelets in the blood, i.e., thrombocytopenia.

Most thrombocytoses result from severe bone marrow damage (myeloproliferative syndromes in particular). Detecting these types of thrombocytoses is essential in order to be able to adopt appropriate medical treatment. An initial analysis of blood platelets and of the percentage of young platelets is a simple procedure that can easily direct exploratory steps, which may include a marrow biopsy analysis, which is a much more invasive procedure.

Two types of thrombocytopenia can be distinguished:
Central, or essential, thrombocytopenia, which results from a defect, in quality and/or number, in megakaryocyte formation and which is expressed as low platelet production and, consequently, low platelet concentration in the blood. Central thrombocytopenia can have different causes which may be genetic in origin, or acquired, such as a vitamin B12 deficiency, some cancers, myelodysplasias, liver damage, or certain treatments such as chemotherapy or radiotherapy. In certain cases, the cause is not identified. Some diseases are known to be related to central thrombocytopenia, such as Bernard-Soulier syndrome or May-Hegglin anomaly (MYH9).
Peripheral thrombocytopenia is characterized by a decrease in circulating platelet counts, a compensatory increase in rnegakaryocytopoiesis, and thus a higher production of platelets. Peripheral thrombocytopenia is generally caused by the destruction of circulating platelets, for example by the action of autoantibodies or antibodies that bind to platelets in the presence of certain medicines (heparins, quinines for example). Peripheral thrombocytopenia is therefore characterized by a higher proportion of young platelets (sometimes called immature platelets). Idiopathic thrombocytopenic purpura (ITP), of autoimmune origin, is the most common cause of peripheral thrombocytopenia, Peripheral thrombocytopenia can also be explained by an inflammatory condition in the patient that may lead to consumption of circulating platelets or be of allergic origin.

Thrombocytopenia can lead to bleeding, visible in the form of petechiae or purpura, abnormal bleeding from the nose and mouth, heavy menstruation, hematomas can also occur.

The treatment of thrombocytopenia depends on its cause. It is therefore essential o be able to distinguish central thrombocytopenia from peripheral thrombocytopenia.

Thrombocytopenia is identified by measuring the number of platelets in the blood, generally by a blood test called a "complete blood count" or "CBC" or "hemogram". Thrombocytopenia is diagnosed if the number of platelets is less than $150 \times 10^9$/L of blood. However, measuring the platelet count alone does not allow the differentiation of central and peripheral thrombocytopenia.

The determination of the amount of young platelets in the blood, i.e., the platelets that have just been produced by the bone marrow, is therefore of particular interest in distinguishing central thrombocytopenia from peripheral thrombocytopenia. Young platelets are distinguished from other circulating platelets by a higher content of large RNA content (messenger and ribosomal RNA) and a slightly larger size. Thiazole orange (TO) or its analogues (e.g., acridine orange), dyes whose fluorescence emission is increased 1000-fold after binding to RNA, are used to discriminate young platelets by flow cytometry. However, the use of TO and its analogues for the analysis of young platelets is tricky, especially in humans where the population of young platelets usually represents only 1 to 2% of the total platelets. Indeed, part of the fluorescence of TO (or its analogues) in platelets is insensitive to treatment with RNase that targets cytosolic RNA, which may be explained by fluorescence after binding to mitochondrial nucleic acids or to nucleotides present in dense granules. Thus, labeling platelets with TO (or its analogues) reveals two populations: a first called "$TO^{bright}$", whose strong fluorescence is drastically reduced by treatment with RNase, and which therefore has a higher RNA content and effectively corresponds to young platelets, a second called "$TO^{dim}$", whose fluorescence of TO (or its analogues) is weaker and is insensitive to RNase treatment, and which therefore contains little or no cytosolic RNA and does not correspond to young platelets.

Despite this limitation, the procedure used to date to identify the cause of thrombocytopenia (i.e., central or peripheral) is based on the use of a TO analogue to determine the proportion of young platelets, called the "immature platelet fraction" or "IPF", in a whole blood sample. It may for example be the process known as Sysmex®. The Sysmex® process uses an algorithm that integrates platelet size and fluorescence in the presence of an acridine orange derivative, a molecule that has properties similar to those of TO with respect to RNAs. This process is used to obtain a percentage of IPF that can be used to make a clinical diagnosis in the face of isolated thrombocytopenia. A high IPF level is considered to reflect peripheral thrombocytopenia while a conventional IPF level measured by the Sysmex method (less than 15%) may reflect central thrombocytopenia. However, as explained above, some of the acridine orange binds to mitochondrial nucleic acids or to nucleotides in dense granules, the latter being insensitive to RNase treatment, which can generate false positives.

There is thus a genuine need for an easy-to-use process that can dispense with the use of thiazole orange (TO) or one of its analogues (e.g., acridine orange) in order to be able to analyze the platelets present in a blood sample in a reliable and reproducible manner, in particular for the in vitro diagnosis of peripheral thrombocytopenia or central thrombocytopenia.

SUMMARY OF THE INVENTION

The inventors demonstrated that flow cytometry measurement of the expression level of major histocompatibility complex class I (MHC I) molecules in the plasma membrane of platelets is correlated with platelet age, a higher level of expression corresponding to "young platelets". Thus, the inventors developed a process to analyze platelets in a blood sample by flow cytometry, using an anti-MHC I alpha chain ligand coupled to a fluorochrome. This analysis process is particularly suitable for distinguishing peripheral thrombocytopenia from central thrombocytopenia.

A first object of the invention relates to a process for analyzing platelets present in a blood sample, said process comprises the steps of:
a) adding to said sample a ligand that binds to MHC I coupled to a fluorochrome;
b) measuring the mean fluorescence intensity of the platelets ($MFI_{platelets}$) with a flow cytometer; and
c) measuring the mean forward scatter (FSC) parameter with said flow cytometer and determining the $MFI_{platelets}$/FSC ratio.

A second object of the invention relates to a process for identifying a population of platelets present in a blood sample, said process comprises the steps of:
a) analyzing platelets present in a blood sample by carrying out the process according to the invention; and
b) using the result of step a) to identify a population of platelets.

A third object of the invention relates to a process for the in vitro diagnosis of peripheral or central thrombocytopenia in a subject comprising the steps of:
a) analyzing platelets present in a blood sample of a subject by carrying out the analysis process according to the invention, or identifying a population of platelets present in a blood sample of a subject by carrying out the identification process according to the invention; and
b) using the result of step a) in the diagnosis of peripheral or central thrombocytopenia.

A fourth object of the invention relates to an in vitro process for monitoring the therapeutic efficacy of a treatment for central or peripheral thrombocytopenia, comprising the steps of:
a) analyzing platelets present in a blood sample of a patient having undergone central or peripheral thrombocytopenia treatment by carrying out the analysis process according to the invention, or identifying a population of platelets present in a blood sample of a patient having undergone central or peripheral thrombocytopenia treatment by carrying out the identification process according to the invention;
b) using the result of step a) in determining the therapeutic efficacy of the treatment of peripheral or central thrombocytopenia.

A fifth object of the invention relates to an in vitro process for prognosing the development of an inflammatory or cardiovascular disease, comprising the steps of:
a) analyzing platelets present in a blood sample of a subject by carrying out the analysis process according to the invention, or identifying a population of platelets present in a blood sample of a subject by carrying out the identification process according to the invention;
b) using the result of step a) in the prognosis of the development of inflammatory or cardiovascular disease.

A sixth object of the invention relates to a kit for implementing a process for diagnosing, for monitoring the therapeutic efficacy of a treatment of, or for prognosing the development of an inflammatory or cardiovascular disease according to the invention, comprising:
a ligand that binds to MHC I coupled to a fluorochrome;
an internal standard; and
instructions.

Figure 1:
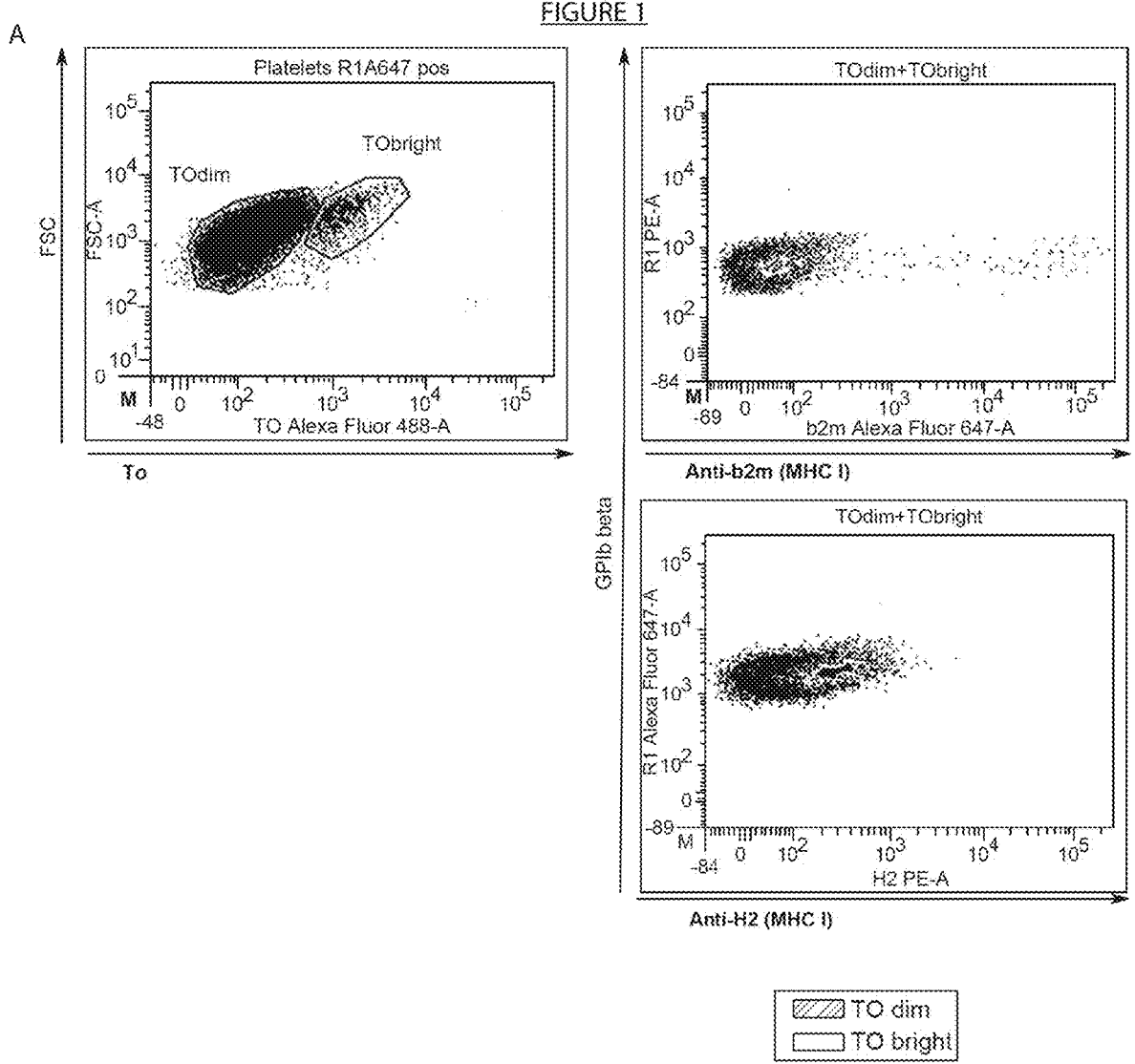
FIG. 1. Surface expression of MHC I molecules is higher on young murine platelets A) Graph of a representative FACS analysis of TO and MHC I expression on murine platelets. The platelets were labeled with a PE or Alexa-647-conjugated anti-GPIb beta antibody and with thiazole orange (TO) (left panel). GPIb beta+ platelets were selected and MHC I expression was analyzed by co-labeling with a PE-conjugated anti-MHC I antibody or an anti-β2m antibody revealed with an Alexa-647-conjugated goat anti-mouse secondary antibody (right panel). $TO^{bright}$ platelets are highlighted in light gray (left and right panels) B) Surface expression of MHC I and GP1bβ molecules was evaluated by calculating the ratio of mean fluorescence intensity (MFI) of MHC I or the MFI of GPIbβ to MFI of the FSC parameter on $TO^{dim}$ or $TO^{bright}$ platelets (* p<0.05, *** p<0.001, ns p>0.05; n=3).
Figure 1:
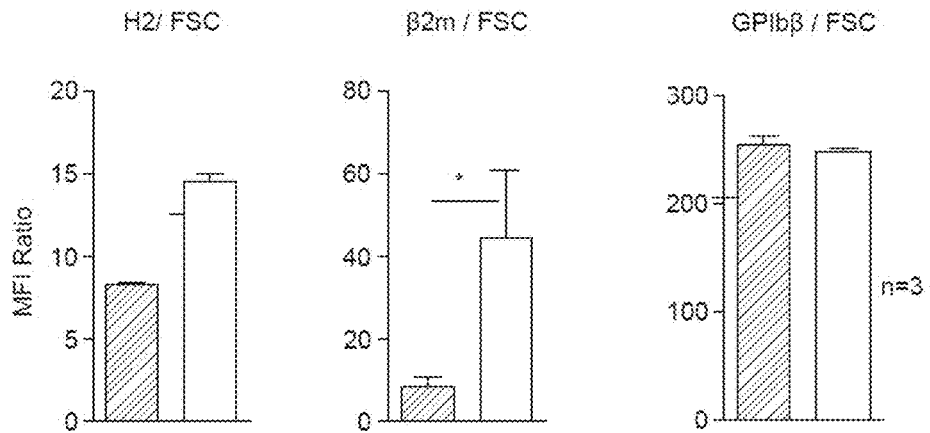

A) Blood samples from healthy donors were tested for TO$^{bright}$ and HLA I$^{high}$ platelet percentages by FACS analysis and MFI percentages with the Sysmex® system (n=6) B) Blood samples from healthy donors or MyH9 deficient patients were analyzed and the MFI of TO and HLA I on the platelets were determined by FACS analysis. The results are expressed as ratios between the MFI of HLA I (W6/32 or β2m) or TO labeling to the FSC MFI. C) FACS graphs of TO labeling on different blood samples before and after RNase treatment. Percentages of TO$^{bright}$ platelets are indicated for each condition. D) Citrated blood samples from healthy donors were activated with 0.1, 0.5, 1, 10, 50 or 100 µM TRAP before the IPF percentages were estimated by Sysmex® (top panel) or the HLA I/FSC or β2m/FSC ratios were analyzed by flow cytometry (bottom panel) (n=3-5).

DETAILED DESCRIPTION

The Applicants have developed a process for analyzing platelets in a blood sample in an accurate and reproducible manner. The use of this process makes it possible, in particular, to determine in vitro the origin (central or peripheral) of thrombocytopenia.

Definitions

"Platelets" are blood cells produced by the fragmentation of megakaryocytes in the bone marrow. Platelets lack a nucleus in mammals and their lifespan in humans is about 7 to 10 days before being removed by macrophages in the spleen or liver. Platelets are essential components of primary hemostasis. In humans, platelets have a diameter of 2 to 4 microns and their normal concentration in the blood is 150 to 400×10$^9$ platelets per liter of blood. Their number tends to decrease with age. Platelets express major histocompatibility complex (MHC) class I molecules on their surface.

The term "young platelets" refers to platelets newly produced by the bone marrow, i.e., platelets less than 24 hours old, for example less than 12 hours.

When the platelet concentration is less than 150×10$^9$ platelets per liter of blood, the platelet level is considered low and is referred to as "thrombopenia" or "thrombocytopenia", at which the risk of bleeding is increased.

When the platelet concentration is greater than 400×10$^9$ platelets per liter of blood, the platelet level is considered high and is referred to as "thrombocytosis", with associated risks of thrombosis.

Two types of thrombocytopenia can be distinguished:
Central, or essential, thrombocytopenia, which results from a defect, in quality and/or number, in megakaryocyte formation and results in low platelet production (blood platelet concentration less than 150×10$^9$ platelets per liter of blood). Central thrombocytopenia can have different causes which may be genetic in origin, or acquired, such as a vitamin B12 deficiency, some cancers, myelodysplasias, liver damage, or certain treatments such as chemotherapy or radiotherapy. In certain cases, the cause is not identified. Some diseases are known to be related to central thrombocytopenia, such as Bernard-Soulier syndrome or May-Hegglin anomaly (MYH9).

Peripheral thrombocytopenia is characterized by a decrease in circulating platelet counts, a compensatory increase in megakaryocytopoiesis, and thus a higher production of platelets, Peripheral thrombocytopenia is generally caused by the destruction of platelets, for example by the action of autoantibodies or antibodies that bind to platelets in the presence of certain medicines (heparins, quinines for example). Peripheral thrombocytopenia is therefore characterized by a higher proportion of young platelets (sometimes called immature platelets). Idiopathic thrombocytopenic purpura (ITP), of autoimmune origin, is a common cause of peripheral thrombocytopenia. Peripheral thrombocytopenia can also be explained by an inflammatory condition in the patient that may lead to consumption of circulating platelets or be of immune origin.

Major histocompatibility complex class I (MHC I) molecules constitute the self-recognition system and present peptide antigens to T lymphocytes. In humans, MHC I is called human leukocyte antigen (HLA) class I. These molecules are expressed at the plasma membrane of almost all nucleated cells and on blood platelets. They consist of the non-covalent association of an alpha chain (comprising 3 immunoglobulin-like domains: α1, α2 and α3) and beta-2 microglobulin (β2m). MHC I expressed at the plasma membrane is always associated with a peptide, which stabilizes MHC I. MHC I is notably involved in the presentation of antigens to CD8 T lymphocytes, making it possible to discriminate self from non-self.

The term "blood sample", as used here, includes any sample containing platelets. A blood sample is, for example, obtained from the blood of a subject. Preferably, it is a whole blood sample, advantageously taken in the presence of anticoagulant according to the best practices of the person skilled in the art, The anticoagulant may be EDTA or citrate.

The term "ligand" within the meaning of the invention denotes a molecule that binds specifically to the target. For example, in the context of the present invention, a ligand that binds to MHC I therefore denotes a ligand that binds specifically to MHC I.

In a particular embodiment of the invention, the ligand is unable to bind to the β2m chain not associated with the alpha chain, i.e., to the soluble β2m chain.

In another particular embodiment of the invention, the ligand is able to bind to the β2m chain not associated with the alpha chain. In this particular embodiment, a sufficiently high concentration of ligand is advantageously used so that the soluble β2m chain present in the blood sample does not interfere with the binding to MHC I when carrying out the process according to the invention.

In a particular embodiment of the invention, the ligand is able to bind to all isotypes of MHC I, i.e., isotypes A (HLA A), B (HLA B) and C (HLA C).

The ligand can be an antibody, an antibody fragment, an aptamer, a protein, a peptide or a small molecule. The ligands that can be used in the context of invention can be easily obtained by the person skilled in the art. Mention may be made, for example, of the Selex process for aptamers or the immunization and cloning processes for antibodies. In a preferred embodiment, the ligand is an antibody or an antibody fragment. Several antibodies that can be used in the invention are commercially available, for example antibody W6/32, produced by the hybridoma ATCC HB-95, for example antibody W6/32 already coupled to APC available from Biolegend, or anti-human β2m antibody already coupled to the fluorophore PE/Cy7 available from Biolegend (item number: 316318).

The term "antibody" is used here in its broadest sense and encompasses various antibody structures that have the desired antigen-binding activity, in particular monoclonal antibodies. These can be human, humanized, chimeric, or non-human species antibodies, for example murine antibodies.

In the context of the present invention, the ligand is coupled to a means allowing its detection in flow cytometry, preferably a fluorochrome (or fluorophore). The term "fluorochrome" refers to a molecule capable of emitting fluorescent light after excitation. The fluorescence intensity (or MFI) emitted by the fluorochrome can be measured by any known means, for example with a flow cytometer capable of detecting and measuring the fluorescence intensity of the fluorochrome.

"Flow cytometry" is a widely used technique that allows particles or cells to move at high speed through a laser beam, counting and characterizing them. Flow cytometry is a particularly advantageous technique because it allows the fluorescence intensity of individual particles, molecules or cells to be measured by passing them one by one in front of a laser beam.

The "internal standard" within the meaning of the invention allows the normalization of fluorescence intensities (MFI) measured in flow cytometry. In the context of the present invention, the internal standard is preferably an element that binds to the ligand. It may in particular be a polystyrene microbead on which the ligand can adsorb. Numerous internal standards adapted to different types of ligands are commercially available, for example the "BD Compbead No. 552843" standard, which can be used when the ligand is an antibody that includes the kappa chain of a mouse antibody.

Within the meaning of the invention, "subject" refers to a mammal, for example a dog, a cat, a sheep, a bovine or a human, preferably the subject is a human. Within the meaning of the invention, "healthy subject" refers a subject who does not present any pathology causing an abnormal blood platelet count and who is not on medication.

The term "diagnosis", is used here in its broadest sense, and is commonly used and well understood by the person skilled in the art. This term designates, for example, the determination of the probability, risk or possibility of having a pathology in a subject.

The term "treatment" or "treat" or "respond to treatment" within the meaning of the invention refers to an improvement, attenuation, reversal or inhibition of the progression of a pathology. In particular, treatment of the pathology may consist of restoring normal platelet production by the bone marrow.

Process for Analyzing Platelets or Identifying a Population of Platelets

The description relates to a process for analyzing platelets present in a blood sample, said process comprises the steps of:
a) adding to said sample a ligand that binds to MHC I coupled to a fluorochrome;
b) measuring the mean fluorescence intensity of the platelets ($MFI_{platelets}$) with a flow cytometer.

The invention relates to a process for analyzing platelets present in a blood sample, said process comprises the steps of:
a) adding to said sample a ligand that binds to MHC I coupled to a fluorochrome;
b) measuring the mean fluorescence intensity of the platelets ($MFI_{platelets}$) with a flow cytometer; and advantageously
c) measuring the mean forward scatter (FSC) parameter with said flow cytometer and determining the $MFI_{platelets}$/FSC ratio.

The applicants indeed found that the level of MHC I expression on the platelet surface correlates with platelet age. Thus, younger platelets express more MHC I on their plasma membrane than older platelets.

In particular, the applicants found that the level of MHC I expression on the surface of the platelets normalized to the FSC parameter correlates with their age. Thus, younger platelets have a higher density of MHC I molecules on their plasma membrane than older platelets.

Step a)

Step a) consists in adding to said sample a ligand that binds to MHC I coupled to a fluorochrome. This step is performed by adding the fluorochrome-coupled ligand to a blood sample, for example under shaking. Shaking is used to homogenize the mixture in order to facilitate contact between the labeled ligands and the platelets.

The incubation time should be sufficient to bring the labeled ligand into contact with the platelets. Typically, the incubation time used by the skilled person is 20 to 30 min for an antibody, but it could be shortened depending on the ligand used and then be less than 5 min, for example less than 4 min, less than 3 min, less than 2 min, less than 1 minute, less than 30 seconds. The incubation time can also be longer than 5 min, longer than 10 min or even longer than 15 min.

The analysis process according to the invention is particularly easy to implement since it can be carried out using a whole blood sample. Nevertheless, it is not limited to the use of a specific blood sample. For example, it may be any fraction of whole blood containing platelets, such as platelet-rich plasma (PRP) or platelets isolated from whole blood. Preferably, the blood sample is a whole blood sample.

In a particular embodiment, the blood sample may contain components other than those naturally present in the blood sample, for example buffers, for adjusting pH, or suitable anticoagulant agents such as EDTA or citrate.

In a particular embodiment, the ligand can be selected from an antibody, an antibody fragment, an aptamer, a protein, a peptide or a small molecule. The appropriate amount of ligand can be easily determined by the experimenter. For example, if the ligand is an antibody, it can be added at a concentration ranging from 0.1 μg/mL to 10 μg/mL. The ligand is added to the sample in saturated condition to ensure proper platelet labeling. In a particular embodiment, the ligand is an antibody or an antibody fragment, for example the W6/32 antibody produced by the hybridoma ATCC HB-95 or a fragment that has retained its ability to bind to MHC I. It may also be an antibody that binds to β2m, in which case a sufficiently high concentration of antibody should be used so that the soluble β2m present in the blood does not interfere with the implementation of the method.

The ligand is coupled to a means allowing its detection with a flow cytometer, preferably a fluorochrome (or fluorophore). The ligand may be coupled to a fluorochrome directly or indirectly, preferably directly. Methods for coupling a ligand with a fluorochrome are widely described in the literature. Coupling therefore presents no particular technical difficulties.

The process is not limited to a particular fluorochrome, as long as it can be detected with a flow cytometer. Advantageously, the fluorochrome is a fluorochrome the excitation and emission wavelengths of which do not interfere with the reagents used to detect RNA. Non-limiting examples of fluorophores are cited below and in the examples: FITC (fluorescein isothiocyanate), PE (R-phycoerythrin), APC (allophycocyanin), PerCP (peridinin chlorophyll protein), PE-CF594, peridinin chlorophyll protein (PerCP)-Cy5.5, PE-Texas Red, GFP (green fluorescent protein), YFP (yellow fluorescent protein) or CFP (cyan fluorescent protein).

Step b)

Step b) consists of measuring the mean fluorescence intensity of the platelets ($MFI_{platelets}$) with a flow cytometer. Of course, the flow cytometer is capable of detecting and measuring the fluorescence of the fluorochrome. The measurement is performed automatically by the flow cytometer. The parameterization of the flow cytometer does not present any particular technical difficulties. In particular, the skilled person will know how to set up the flow cytometer according to the chosen fluorochrome.

The measurement performed in step b) allows the identification of platelets bound by the labelled ligand, and allows the identification of one or more population(s) of platelet(s), particularly a population of young platelets.

Step c)

Step c) consists in measuring the mean forward scatter (FSC) parameter with said flow cytometer and determining the $MFI_{platelets}/FSC$ ratio. In addition to fluorescence intensity, the flow cytometer can measure other parameters that can give an indication of particle size, for example platelet size. The parameter most commonly measured to give an indication of platelet size is forward scatter (FSC), also referred to hereafter as "$FSC_{platelets}$". This can be FSC-A, FSC-H or FCS-W. FSC-A is generally used.

In a particular embodiment, the $MFI_{platelets}$ measurement is normalized to the mean fluorescence intensity of an internal standard ($MFI_{standard}$) in order to obtain a mean fluorescence intensity of normalized platelets ($MFI_{normalized\ platelets}$). The internal standard is preferably added to said sample in step a), either before or after the ligand, or simultaneously with the ligand, preferably before the ligand. The amount of appropriate internal standard can be easily determined by the experimenter, preferably by putting it in an amount of the same order of magnitude as the number of platelets.

Normalization of the $MFI_{platelets}$ measurement to an internal standard is particularly advantageous since it overcomes inter-experimental, inter-laboratory and/or inter-experimenter variability.

In a particular embodiment, the internal standard binds to the fluorochrome-coupled ligand, for example the fluorochrome-coupled ligand adsorbs on the internal standard. In this particular embodiment, the $MFI_{standard}$ is therefore the mean fluorescence intensity emitted by the fluorochrome bound to the standard and measured with the flow cytometer capable of detecting and measuring the fluorescence of the fluorochrome. The flow cytometer should be adjusted to distinguish between the labeled platelets and the labeled internal standard. In general, the distinction is made by size. When the distinction is made by size, it is therefore essential that the size of the labeled standard is chosen so that the standard can be easily distinguished from the platelets.

Advantageously, the internal standard is a polystyrene microbead on which the fluorochrome-coupled ligand is adsorbed. It can be, for example, a polystyrene microbead coated with antibodies that bind to said fluorochrome-coupled ligand. Mention may be made, for example, of the commercial product "BD Compbead No. 552843" which can be used when the ligand is an antibody that includes the kappa chain of a mouse antibody (e.g., a chimeric antibody).

In a preferred embodiment, the process of the invention further comprises a step c) measuring the mean FSC diffusion parameter (FSC) with said flow cytometer and determining the $MFI_{platelets}/FSC$ or $MFI_{normalized\ platelets}/FSC$ ratio. The determination of the $MFI_{platelets}/FSC$ or $MFI_{normalized\ platelets}/FSC$ ratio is particularly advantageous since it allows for a finer analysis of the platelets. This makes it possible to more finely differentiate between one or more populations of platelets, especially a population of young platelets. Step c) is performed automatically by the flow cytometer simultaneously with step b). In this particular embodiment, the determination of ratios can be done automatically with the values measured by the flow cytometer. The ratio $MFI_{normalized\ platelets}/FSC$ can, for example, be obtained by calculating the $(MFI_{platelets}/FSC_{platelets})/(MFI_{standard}/FSC_{standard})$ ratio. As with $FSC_{platelets}$ which gives an indication of the platelet size, the $FSC_{standard}$ parameter gives an indication of the standard particle size.

The invention also relates to a process for identifying a population of platelets, preferably a population of young platelets, present in a blood sample, said process comprises the steps of:

a) analyzing platelets present in a blood sample by carrying out the process according to the invention; and b) using the result of step a) to identify a population of platelets, preferably a population of young platelets.

Identification of the platelet population is done automatically by the flow cytometer according to the parameters described above.

Diagnostic Process

The invention relates to a process for the in vitro diagnosis of peripheral or central thrombocytopenia in a subject comprising the steps of:

a) analyzing platelets present in a blood sample of a subject by carrying out the process for analyzing platelets according to the invention; and b) using the result of step a) in the diagnosis of peripheral or central thrombocytopenia.

The result obtained by analyzing platelets according to the invention allows a diagnosis of peripheral thrombocytopenia in a subject. In particular, a positive diagnosis of peripheral thrombocytopenia is given by an increase in said subject of the parameter(s) $MFI_{platelets}$, $MFI_{normalized\ platelets}$, the $MFI_{platelets}/FSC$ ratio and/or the $MFI_{normalized\ platelets}/FSC$ ratio relative to the same parameter(s) measured in a healthy subject.

An increase in the abovementioned parameter(s) in the subject under considered in comparison with the same parameter(s) measured in a healthy subject, reflects an increase in the amount of young platelets in said subject considered and demonstrates increased bone marrow activity and therefore allows the diagnosis of peripheral thrombocytopenia.

In a preferred embodiment, the increase in one or more of the above-mentioned parameters is of the order of a factor greater than 1.5, for example greater than 2, greater than 2.5, greater than 3, or greater than 3.5.

The result obtained by analyzing platelets according to the invention allows a diagnosis of central thrombocytopenia in a subject. In particular, a positive diagnosis for central thrombocytopenia is given by the parameter(s) $MFI_{platelets}$, $\text{MFI}_{normalized\ platelets}$, $\text{MFI}_{platelets}/\text{FSC}$ ratio and/or $\text{MFI}_{normalized\ platelets}/\text{FSC}$ ratio in said subject similar or identical to the same parameter(s) measured in a healthy subject.

In a particular embodiment, said subject has previously been diagnosed as having thrombocytopenia or as being likely to have thrombocytopenia. The diagnostic process according to the invention will then make it possible to know the origin (central or peripheral) of the thrombocytopenia.

Process for Monitoring the Therapeutic Efficacy of a Treatment

The invention also relates to an in vitro process for monitoring the therapeutic efficacy of a treatment for central or peripheral thrombocytopenia, comprising the steps of:

a) analyzing platelets present in a blood sample of a patient having undergone treatment for central or peripheral thrombocytopenia by implementing the analysis process according to the invention;

b) using the result of step a) in determining the therapeutic efficacy of the treatment of central or peripheral thrombocytopenia.

Prognostic Process

The invention also relates to an in vitro process for prognosing the development of an inflammatory or cardiovascular disease, comprising the steps of:

a) analyzing platelets present in a blood sample of a subject by implementing the analysis process according to the invention;

b) using the result of step a) in the prognosis of the development of inflammatory or cardiovascular disease.

In a particular embodiment, the inflammatory disease is sepsis. In another particular embodiment, cardiovascular disease is atherosclerosis.

Diagnostic Kit

The invention also relates to a kit for diagnosing peripheral thrombocytopenia or central thrombocytopenia in a subject, for monitoring the therapeutic efficacy of a treatment or for prognosing the development of an inflammatory or cardiovascular disease, comprising:

a ligand that binds to MHC I coupled to a fluorochrome;

an internal standard; and instructions for implementing an in vitro diagnostic process according to the invention.

Treatment Method

The invention also relates to a method for treating peripheral thrombocytopenia or central thrombocytopenia in a subject, comprising:

implementing an in vitro diagnostic process according to the invention; and when the diagnosis is positive, initiating appropriate treatment of the subject.

Appropriate treatments are in particular described in reference [8], incorporated by reference into the present application, in particular the sections "First-line therapy", "Second-line therapy", "Third-line therapy", "Other new agents" and Table 2 on pages 18 and 19.

EXAMPLES

Materials and methods

Reagents

The reagents are commercially available. Thiazole orange (TO) is from Sigma-Aldrich. Xylazine (Rompun®) and ketamine (Imalgene 1,000®) are from Bayer and Merial, respectively. Biotin is supplied by ThermoFischer and diphtheria toxin (DT) by Santa Cruz.

Antibodies and Flow Cytometry

The rat monoclonal antibody against the extracellular domain of the platelet glycoprotein GPIb beta (Ram1, [7]) was produced and coupled to Alexa647 or 488 in our laboratory. Anti-HLAI mouse antibodies (clone W6/32) coupled to allophycocyanin (APC) (item number: 311410), human anti-β2m coupled to PE-CY7 (item number: 316318) and human anti-CD45 coupled to APC-cy7 (clone 2D1) (item number: 358515) are from Biolegend. Mouse anti-H2 (done M1/42) coupled to phycoerythrin (PE) (item number: 125506) and streptavidin coupled to APC-CY7 (item number: 405208) were purchased from Biolegend. Mouse (clone S19.8) anti-b2 microglobulin antibody (β2m) (item number: 555299) is from BD Pharmingen. Mouse anti-CD45 antibody coupled to PE-cy7 (clone 30-F11) (item number: 25-0451) was supplied by Invitrogen. Human anti-ribosomal P protein antibody was kindly provided by Prof. Sun, National Yang-Ming University, Taiwan [1].

Whole blood was diluted in 10 volumes of PBS containing 1% BSA and 6 mM EDTA. Fcγ receptors were blocked by the "FcR blocking" reagent (Milteny Biotec) diluted 1/200 before labeling with the antibody or antibodies. After a washing step, the cells were counter-labeled with 1 µg/ml TO in PBS for 15 min. The samples were then diluted in 20 volumes of 1% paraformaldehyde and analyzed by flow cytometry (LSRFortessa™ cell analyzer, BD Biosciences) within 45 minutes. The data were analyzed with the BD FACSDiva software.

Mice

The experiments were performed on 8- to 10-week-old C57Bl6/J mice purchased from Charles River Laboratories. Mice positive for both diphtheria toxin receptor transgenes and PF4—designated in the text by PF4-cre/iDTR—were generated as previously described [2].

Platelet Transfusion

PF4-cre/iDTR mice were rendered severely thrombocytopenic by injection of diphtheria toxin (DT) (100 ng/day, i.p.) for 4 days. 8 days after the last injection, blood was drawn from the abdominal aorta of the anesthetized mice on citrate (3.8%) used as anticoagulant and the platelets were isolated as previously described [3]. The washed crosslinked platelets were biotinylated, resuspended at $1.2.10^6/\mu L$ and 150 µL of the suspension was injected into the retroorbital sinus of WT mice. Blood samples were collected 5 minutes after transfusion (time 0) and 30 min, 2 h, 24, 48 and 72 h after.

Ethical Statement

Human blood samples were obtained from voluntary and unpaid donors recruited by the Etablissement Français du Sang—Grand Est (EFS-Alsace), where the research was carried out. At each blood collection, the donors signed an informed consent indicating that the samples could be used for research purposes. The ethical approval of the animal experiments was in accordance with European Union Directive 2010/63/EU. The study was approved by the Comité régional d'éthique pour l'expérimentation animale de Strasbourg, C.R.E.M.E.A.S. (CEEA 35).

Statistical Analyses

The statistical analyses were done using the GraphPad software (Prism 5.02).

Results

Young Murine Platelets Express More MHC I Molecules on Their Surface

First, we analyzed whether the expression of class I molecules on the surface of mouse platelets was dependent on their age. In mice, thiazole orange (TO) labeling allows two platelet populations to be easily discriminated, about 10% of which show a strong TO fluorescence ($TO^{bright}$) (FIG. 1A, left) and are less than 12 hours old [2]. The expression of MHC I molecules on the platelet surface was estimated by flow cytometry after labeling with an anti-β2m or anti-MHC I (H2) antibody followed by TO labeling. The expression of class I molecules appeared to be higher on $TO^{bright}$ platelets than on $TO^{dim}$ platelets (FIG. 1A, right). To exclude the fact that younger platelets may express more MHC I molecules due to their larger size, we calculated the ratio of the mean fluorescence intensity (MFI) of the β2m or heavy chain (H2) labeling to the mean FSC parameter (a parameter correlated to cell size) in both $TO^{dim}$ and $TO^{bright}$ populations (FIG. 1B). The ratio was significantly higher in the $TO^{bright}$ population than in the $TO^{dim}$ platelet population (H2/FSC ratio 14.55+/−0.46 in $TO^{bright}$ vs 8.35+/−0.14 in $TO^{dim}$; p<0.001 and β2m/FSC ratio 44.78+/−16.50 in $TO^{bright}$ vs 8.25+/−2.32 in $TO^{dim}$; n=3; p<0.05). In contrast, when we analyzed the expression of GPIbβ, a major platelet-specific glycoprotein, the ratio was similar for both platelet populations (GPIb/FSC ratio 247.07+/−3.57 in $TO^{bright}$ vs 254.70+/−8.15 in $TO^{dim}$; n=3; ns).

On the whole, these data showed that under homeostatic conditions, young murine platelets express more MHC I molecules on their surface.

Surface Expression of Class I Molecules Decreases In Vivo as Platelets Age

Figure 2:
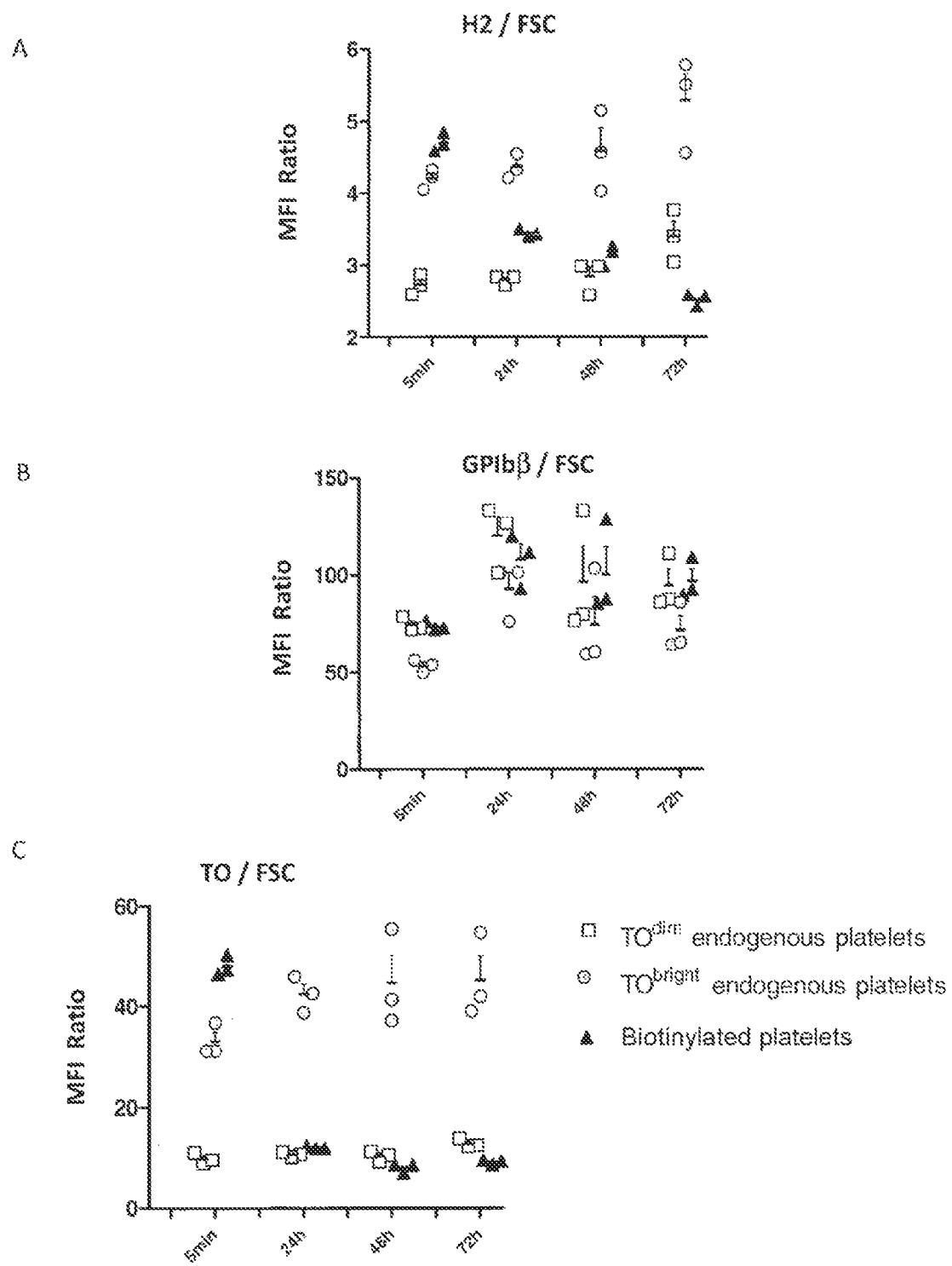
FIG. 2. Surface expression of MHC I rmolecules decreases in vivo during platelet aging.
Platelets from iDTR PF4 cre mice treated with diphtheria toxin (DT) were isolated, biotinylated and transfused to WT mice. Flow cytometric analysis of A) MHC I expression B) GPIbβ expression and C) TO labeling on biotinylated transfused platelets (▲) and endogenous $TO^{dim}$ (□) or $TO^{bright}$ (✻) platelets 5 min, 24 h, 48 h and 72 h post-transfusion. Results expressed as ratios between the MFI of the labeling and the MFI of the FSC parameter (n=3, a representative of 3 independent experiments).

We then determined whether the surface expression of MHC I on platelets was affected by their aging in vivo. We took advantage of iDTR PF4 cre mice to obtain a population of young synchronous platelets [2] Daily administration of diphtheria toxin (DT) for 4 days induced ablation of mature megakaryocytes, blocking platelet production and leading to progressive thrombocytopenia. Four days after stopping treatment (the $8^{th}$ day), megakaryopoiesis and thrombopoiesis were significantly improved, resulting in the transient presence of a vast majority of young platelets (data not shown and [2]). Thus, platelets from DT-treated iDTR PF4 cre mice were isolated on the $8^{th}$ day, biotinylated and transfused to WI mice. MHC I expression on biotinylated transfused platelets was analyzed and compared with MHC I expression on endogenous platelets by flow cytometry at different times after transfusion. The results showed that the (TO mean fluorescence)/(mean FSC) ratio was high for the biotinylated platelets 5 min after transfusion and comparable to endogenous $TO^{bright}$ platelets. 24 h later, it was equal to that of endogenous $TO^{dim}$ platelets (FIG. 2C), confirming the in vivo aging of the transfused platelets. Remarkably, MHC I expression on biotinylated transfused platelets gradually decreased over time. Five minutes after transfusion, MHC I expression on biotinylated platelets was similar to the level of expression on endogenous $TO^{bright}$ platelets. Twenty-four hours later, this level of expression decreased significantly to the same level of expression as on endogenous $TO^{dim}$ platelets (FIG. 2A). This experiment shows that in vivo, the level of expression of MHC I molecules on the surface of platelets is related to their age. In contrast, GPIbβ expression was stable on transfused platelets over a period of 72 hours (FIG. 2B).

On the whole, these data highlighted the relevance of the MHC I expression parameter in discriminating young platelets less than 24 h old.

Figure 3:
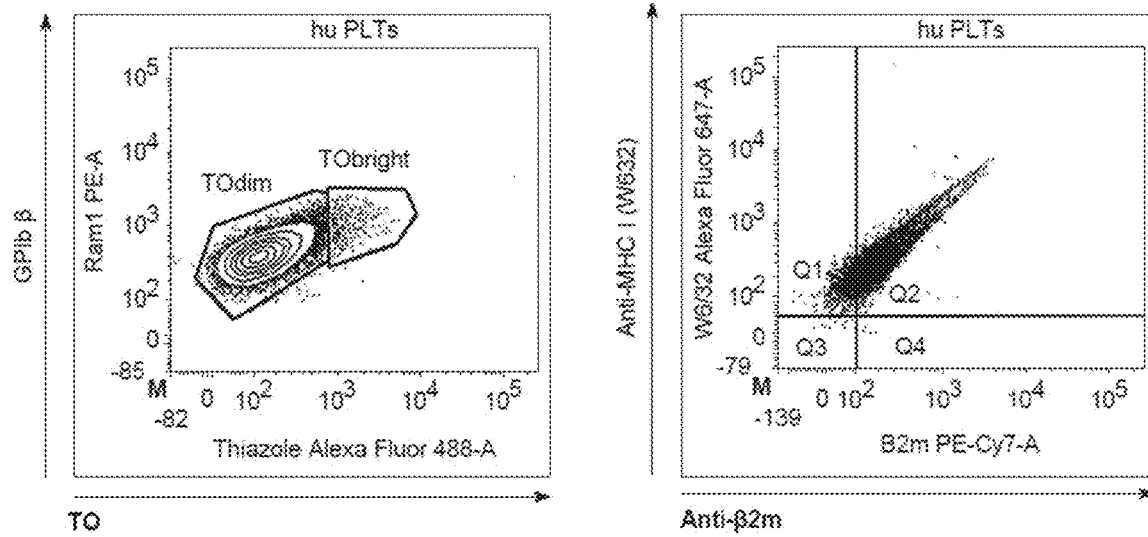
FIG. 3. HLA I molecules are preferentially expressed by highly fluorescent human platelets for thiazole orange A) Representative FACS graphs of TO and MHC I expression on human platelets. Platelets were labeled with PE-conjugated anti-GPIb and TO (left panel). GPIbβ+ platelets were selected and MHC I expression was analyzed by staining with an A647-conjugated anti-MHC I and a PE-CY7-conjugated anti-β2m antibody (right panel). The $TO^{bright}$ platelets are highlighted in light gray (left and right panels). B) The cell surface expression of MHC I and GP1bβ molecules was evaluated by calculating the ratio between the MHC I MFI (anti-β2m or anti-HLA I labeling) or the GPIbβ MFI and the FSC parameter MFI on $TO^{dim}$ or $TO^{bright}$ platelets (* p<0.05, ** p<0.01, ns p>0.05; n=7).
Figure 3:
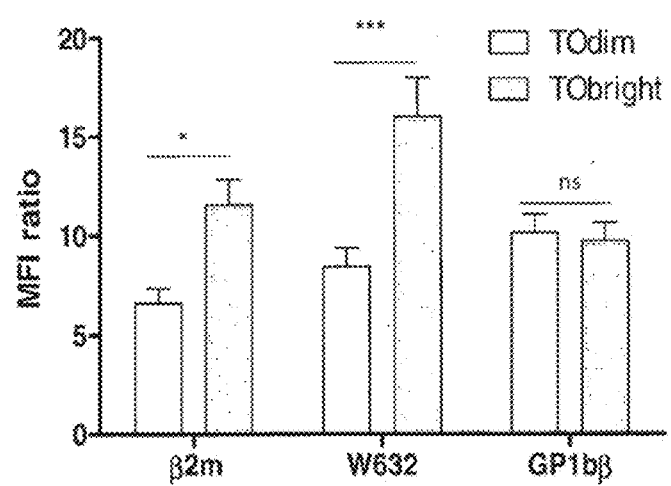

HLA I Molecules are Preferentially Expressed by $TO^{bright}$ Human Platelets In humans, $TO^{bright}$ platelets represent 1 to 2% of the total platelet population (FIG. 3A, left panel). To characterize the expression of HLA I molecules on the surface of human platelets, the latter were co-labeled with an anti-β2m antibody, a pan anti-HLA class I antibody, W6/32 [4]—followed by counter-labeling with TO. Flow cytometry analysis revealed that, as observed in mice, $TO^{bright}$ platelets expressed higher levels of HLA I molecules (FIG. 3A, right panel, highlighted in gray).

To analyze the distribution of HLA I molecules in the platelet population independently of platelet size, we used the same approach as for murine platelets, i.e., the ratio of HLA I MFI/FSC parameter (FIG. 3B). Again, we found that this ratio was higher in $TO^{bright}$ platelets than in $TO^{dim}$ platelets (β2m/FSC ratio 11.58±1.25 in $TO^{bright}$ versus 6.59±0.762 in $TO^{dim}$, n=7, p<0.05 and W632/FSC ratio 16.02±1.99 in $TO^{bright}$ versus 8.46±0.93 in $TO^{dim}$, n=7, p<0.001). Conversely, the GPIbβ MFI/FSC ratios were similar between $TO^{dim}$ and $TO^{bright}$ highlighting the particularity of HLA I molecule expression on young platelets.

Human Platelets that Strongly Express HLA I Molecules have a Higher Ribosomal Protein Content, a Characteristic of Young Platelets The ribosomal P protein antigen is present on the C-terminal part of 3 ribosomal subunits (RLP0, 2 and 3) which are necessary for mRNA translation [5]. Since mRNA translation occurs primarily in the first few hours of life of a platelet [2], it would be expected to detect the ribosomal P protein antigen at least in $TO^{bright}$ platelets.

Figure 4:
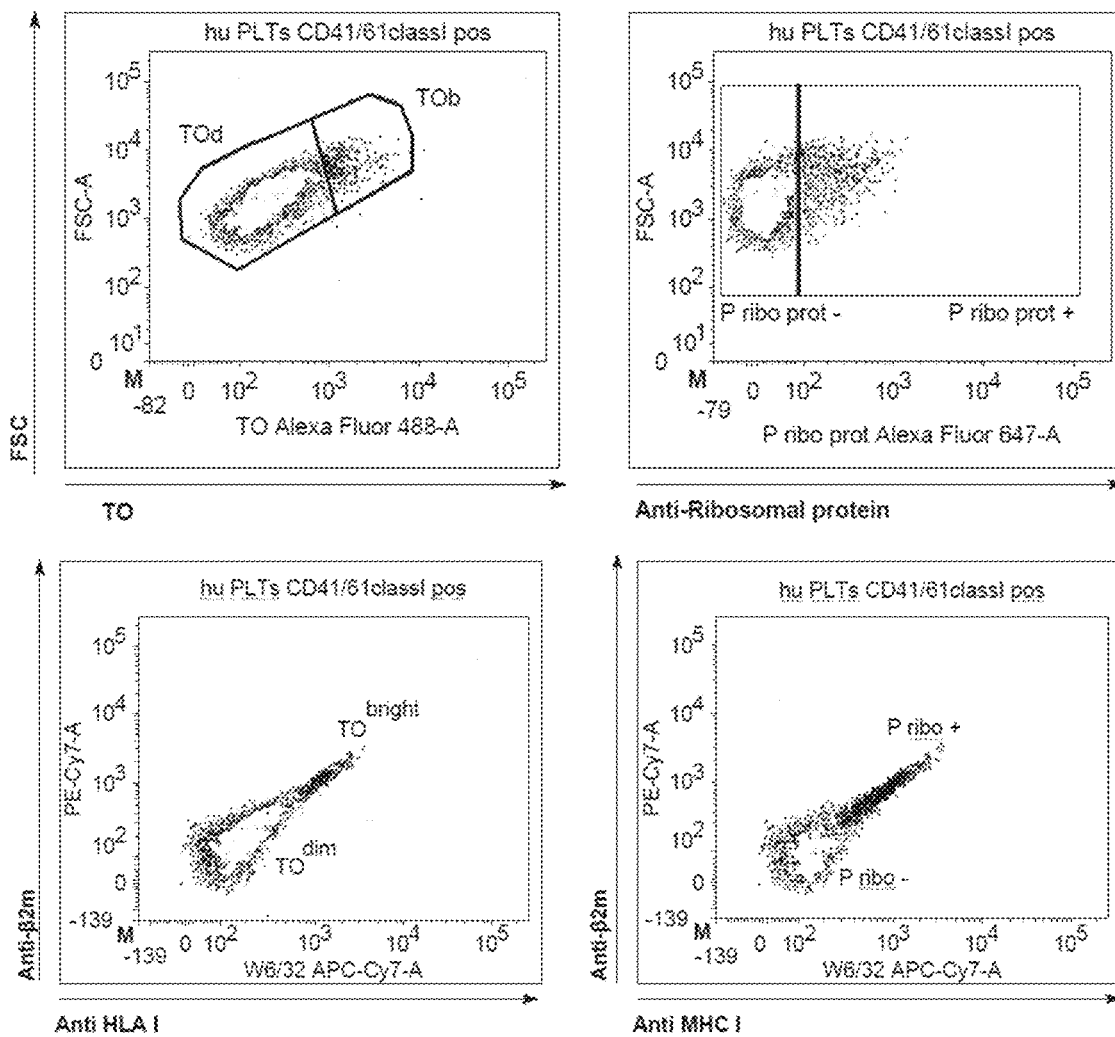
FIG. 4. Human platelets expressing a high density of MHC I molecules exhibit characteristics of young platelets.
Representative FACS graphs of ribosomal protein expression, TO and MHC I molecule expression on human platelets. Human platelets were fixed, permeabilized, co-labeled with a PE-conjugated anti-GPIb, a rnAb ribosomal P protein antibody, an A647-conjugated anti-MHC I, a PE-CY7-conjugated anti-β2m antibody, and TO and then analyzed by FACS. A) GPIbβ+ platelets were selected, Ribosomal protein expression was analyzed by highlighting $TO^{bright}$ platelets in dark gray (top right panels). The expression of MHC I molecules was analyzed by highlighting the TO$^{bright}$ or P-ribosomal high platelets in dark gray (bottom panels). B) Analysis of the distribution of ribosomal P protein or TO$^{bright}$ labeling in populations strongly or weakly expressing HLA I molecules.
Figure 4:
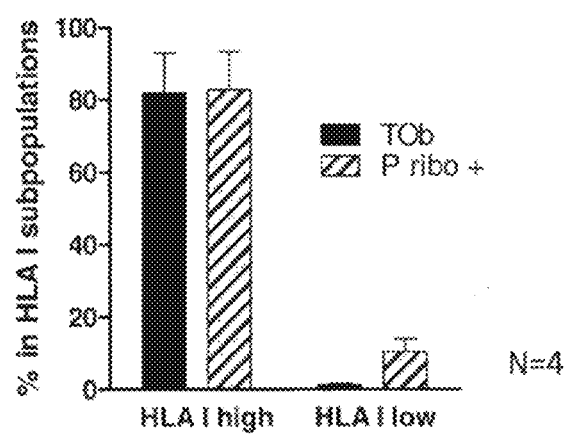

Human platelets were fixed, permeabilized, and co-labeled with antibody against ribosomal P protein antigen, an anti-β2m antibody, a pan anti-HLA I antibody, W6/32, and TO before being analyzed by flow cytometry (FIG. 4A).

Labeling with antibody against ribosomal P protein revealed that 13.3±% (n=4) of the human platelets expressed this protein while 83±% (n=4) in the $TO^{bright}$ platelet sub-population, indicating that this antigen was more expressed by younger platelets. Furthermore, analysis of MHC I molecule expression showed an increased presence on TO$^{bright}$ or ribosomal P-high platelets in dark gray (bottom panels). We then analyzed the distribution of ribosomal P protein in populations with high or low expression of HLA I molecules (labeled with W6/32 or anti-β2m). As shown in FIG. 4B, ribosomal P protein was expressed in most HLA I$^{high}$ platelets but only in a minority of HLA I$^{low}$ platelets (82.77±10.63%, 10.47±3.59%, respectively, n=4) (FIG. 4B).

Figure 5:
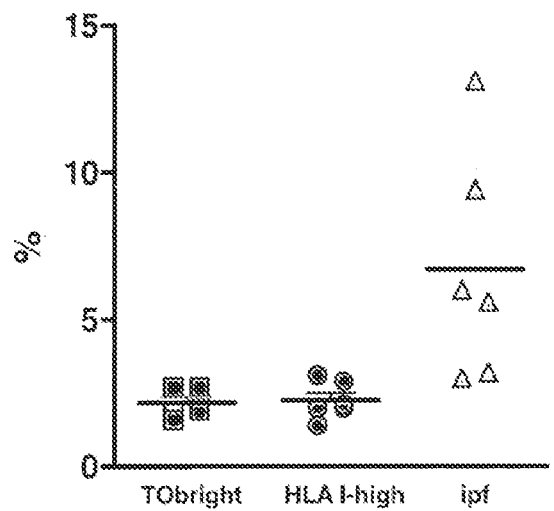
FIG. 5. Cell surface expression of MHC I is a reliable criterion for determining the proportion of young platelets in patients.
Figure 5:
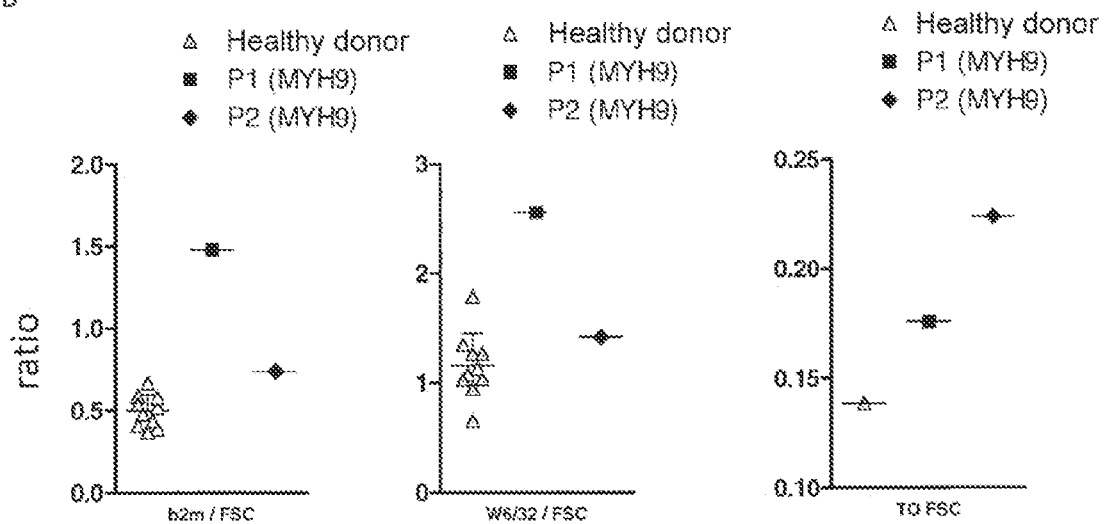
Figure 5:
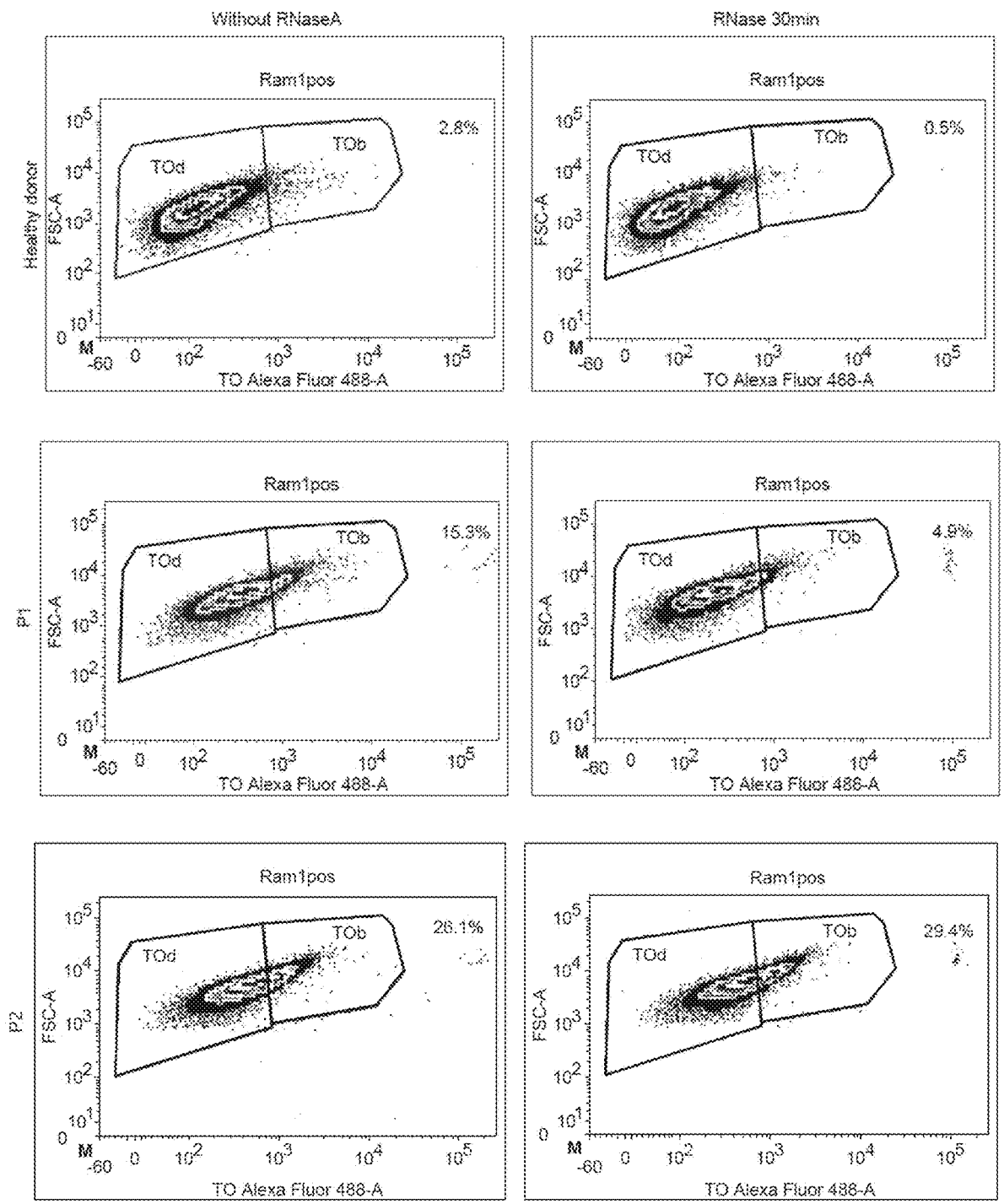
Figure 5:
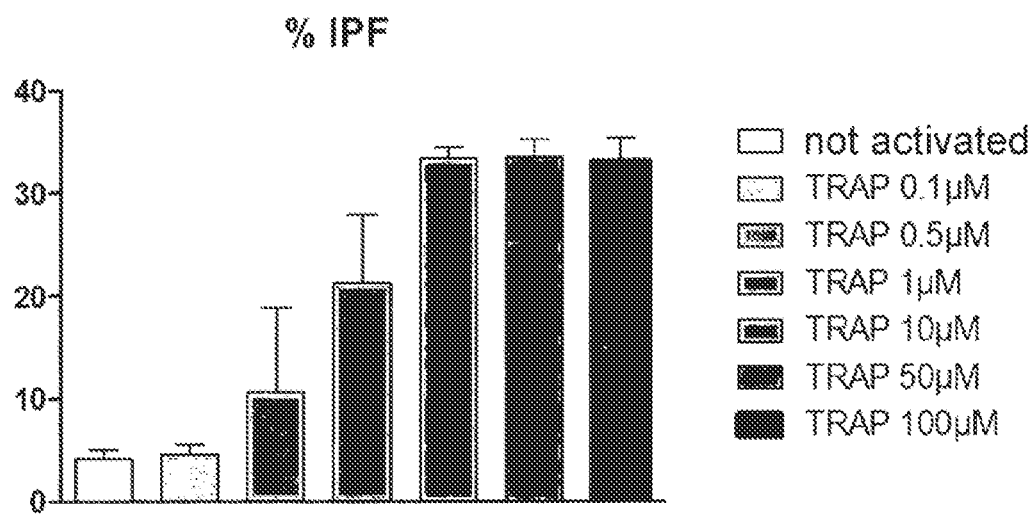
Figure 5:
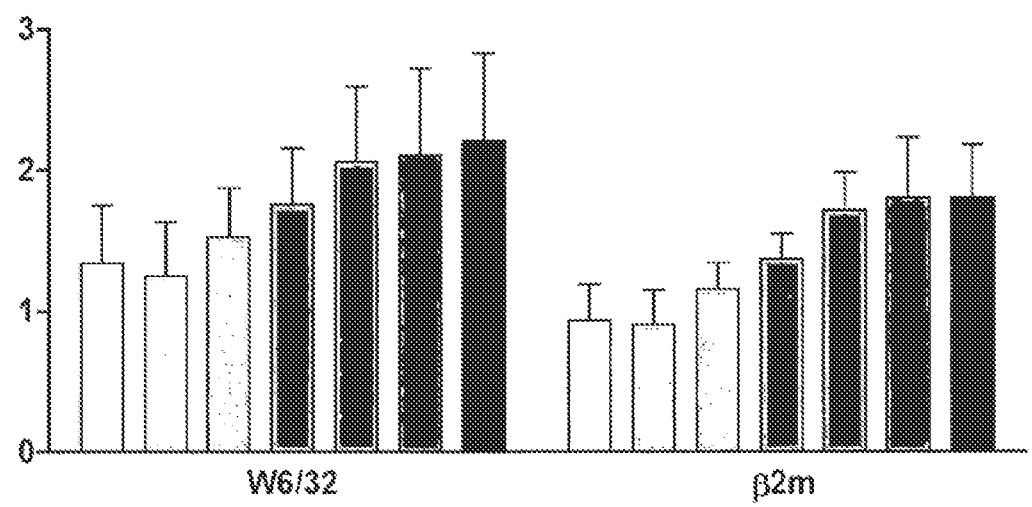

The Level of Expression of HLA I Molecules on Platelets Can be Used as a Criterion to Assess the Proportion of Young Platelets in a Patient To study the relevance of these observations in clinical applications, we evaluated the expression of HLA I molecules on the surface of human platelets from healthy donors or patients with pathologies associated with an increase in the proportion of young platelets in the circulation. We first compared the percentage of "HLA I$^{high}$" and TO$^{bright}$ platelets to the percentage of IPF donated by Sysmex® in healthy volunteers (FIG. 5A, n=6). While the percentage of HLA I$^{high}$ and TO$^{bright}$ platelets were similar (2.25%±0.26 vs 2.17%±0.19, n=6), the percentage of IPF was more heterogeneous but still less than 15% in healthy volunteers (6.7%±1.6, n=6).

Finally, we analyzed the expression of HLA I molecules on the surface of the platelets of two patients with a myosin 9 defect whose Sysmex® analysis showed a high percentage of IPF (64.9 and 42.7% IPF, respectively).

Each patient's citrated blood was co-labeled with an antibody against β2m, a pan anti-HLA I antibody, W6/32, and TO before being analyzed by flow cytometry. Remarkably, only one patient (P1) had high ratios of β2m/FSC and W6/32/FSC compared with the control although the TO/FSC ratio was higher in both patients (P1 and P2) compared with the healthy volunteer (FIG. 5B). Considering the fact that TO can bind not only RNA but also the contents of granules, RNaseA treatment was performed prior to TO labeling. Flow cytometry analyses showed that RNaseA treatment significantly decreased the proportion of TO$^{bright}$ platelets in patient 1 (4.9% TO$^{bright}$ after RNaseA treatment vs 15.9% TO$^{bright}$ before RNaseA treatment) whereas this treatment did not affect the TO$^{bright}$ platelet population in patient 2 (26.1% TO$^{bright}$ after RNaseA treatment vs 29.4% TO$^{bright}$ before RNaseA treatment) (FIG. 5C).

Since the estimation of IPF is known to be potentially biased by platelet activation, notably due to the presence of aggregates [6], we have verified whether the surface expression of HLA I molecules could be a more reliable criterion for assessing the proportion of young platelets.

Citrated blood was therefore incubated with different concentrations of a platelet aggregation reagent, TRAP (0.1, 0.5, 1, 10, 50 or 100 μM), before being analyzed by flow cytometry or with Sysmex® technology. While from 0.5 μM TRAP, a significant increase in IPF with Sysmex® technology was observed, (10.7±8% IPF for the 0.5 μM TRAP condition vs 4.2±0.8% IPF for the non-activated condition; n=3), the β2m/FSC or W632/FSC ratios remained stable (1.3±0.4 in the 0.5 μM TRAP condition vs 1.5±0.3 in the non-activated condition, n=3). It was noted that with higher doses of TRAP (100 μM), the HLA I/FSC ratio was increased, which may be due to exposure to the plasma membrane of the HLA I complexes present in the granules (FIG. 5D). However, it is interesting to stress that this increase remained within the reference values found in healthy volunteers.

These data suggest that the level of expression of HLA I molecules is more reliable than TO labeling or Sysmex® technology for detecting patient samples with high proportions of young platelets.

Interest of Normalization to FSC (FSC-A)

a) Blood samples from 7 healthy donors and one patient with Bernard-Soulier syndrome were analyzed with the process according to the invention, optionally calculating a ratio with FSC (i.e., with and without FSC normalization). The results are presented in FIG. 6. With regard to the results obtained without normalization, the BSS patient would be suffering from peripheral thrombocytopenia. Indeed, the data without normalization seem to show that the BSS patient's platelets express more HLA I molecules on their surface. This patient would therefore have more young platelets than healthy donors.

Calculation of a ratio with FSC shows that the BSS patient's platelets do not express more HLA I molecules on their surface. The BSS patient therefore has no more young platelets than healthy donors. Normalization therefore avoids a false positive.

b) Blood samples from 21 healthy donors, one patient with myelofibrosis (MF), two patients with May-Hegglin anomaly (MYH9) and two patients with thrombocytopenic thrombotic purpura (ITP) were analyzed with the process according to the invention, optionally calculating a ratio with FSC (i.e., with and without FSC normalization). The results are presented in FIG. 7.

Without reference to platelet size, all of the patients would be suspected of having more young platelets and would therefore be labeled "peripheral thrombocytopenia", This finding is consistent with the pathology of MF and ITP (increased bone marrow activity) patients, whereas MYH9 patients may not have increased marrow activity.

The ratio to platelet size shows that the MYH9 2 patient is in fact a false positive with no more young platelets than healthy donors.

Discussion

The results showed that measuring the level of MHC I expression in flow cytometry in relation to platelet size is useful for platelet analysis, particularly for identifying young platelets. It was indeed shown that young platelets express more MHC I on their surface, this level decreases with the age of the platelet. All these results highlight the interest of the MHC I/FSC ratio in evaluating the proportion of young platelets in a subject.

To date, clinicians generally visualize RNA labeling with TO to analyze young platelets present in a sample (TO$^{bright}$). But this technique has limitations given that the reagent used to bind cytosolic RNA (TO) can also bind nucleotides contained in the granules. The measurement of MHC I expression avoids non-specific labeling of the RNA.

Furthermore, the measurement of MHC I expression avoids another disadvantage, which is the presence of aggregates in the analyzed sample, which generate false positives with the Sysmex® process.

The results obtained by the inventors were particularly accurate when the measurement of the MHC I expression level, by measuring the parameter MFI$_{platelets}$, was normalized to the FSC parameter, making it possible, in particular, to give an indication of the particle size, for example of the size of the platelets, and then to the fluorescence intensity of an internal standard (MFI$_{standard}$). This normalization in particular makes it possible to compensate for inter-experimental, inter-laboratory and/or inter-experimenter variability. Even more accurate results were obtained when the inventors analyzed the platelets by determining the ($MFI_{platelets}/FSC_{platelets})/(MFI_{standard}/FSC_{standard})$ ratio (i.e., $MFI_{normalized\ platelets}/FSC$). This ratio allows the platelets to be analyzed with remarkable finesse. Ultimately, it allows for a finer differentiation between one or more populations of platelets, especially a population of young platelets. In conclusion, the level of MHC I expression measured in flow cytometry is a good marker for analyzing the platelets present in a blood sample, particularly for determining the proportion of young platelets. The expression density of MHC I molecules thus constitutes a marker of choice for diagnosing peripheral or central thrombocytopenia in a subject and for monitoring the therapeutic efficacy of a treatment for central or peripheral thrombocytopenia.

REFERENCES CITED IN THE APPLICATION AS "[REFERENCE NUMBER]"

1. Sun, K. H., et al., *Monoclonal antibodies against human ribosomal P proteins penetrate into living cells and cause apoptosis of Jurkat T cells in culture*. Rheumatology (Oxford), 2001. 40 (7): p. 750-6.
2. Angenieux, C., et al., *Time-Dependent Decay of mRNA and Ribosomal RNA during Platelet Aging and Its Correlation with Translation Activity*. PLoS One, 2016. 11 (1): p. e0148064.
3. Hechler, B., et al., *Platelets are dispensable for antibody-mediated transfusion-related acute lung injury in the mouse*. J Thromb Haemost, 2016. 14 (6): p. 1255-67.
4. Tran, T. M., et al., *The epitope recognized by pan-HLA class I-reactive monoclonal antibody W6/32 and its relationship to unusual stability of the HLA-B27/beta2-microglobulin complex*. Immunogenetics, 2001. 53 (6): p. 440-6.
5. Derylo, K., et al., *The uL10 protein, a component of the ribosomal P-stalk, is released from the ribosome in nucleolar stress*. Biochim Biophys Acta, 2018. 1865 (1): p. 34-47.
6. Miyazaki, K., et al., *Immature platelet fraction measurement is influenced by platelet size and is a useful parameter for discrimination of macrothrombocytopenia*. Hematology, 2015. 20 (10): p. 587-92.
7. Perrault, C. et al., *Novel Monoclonal Antibody against the Extracellular Domain of GPIbModulates vWF Mediated Platelet Adhesion*, Thromb Haemost, 2001. 86: p. 1238-48.
8. Nomura, S., *Advances in Diagnosis and Treatments for Immune Thrombocytopenia*, Clinical Medicine Insights: Blood Disorders, 2016. 9: p. 15-22.

The invention claimed is:

1. A process for analyzing platelets present in a blood sample, said process comprises the steps of:
   a) obtaining a fluorochrome-coupled ligand that binds to MHC I expressed on said platelets present in said blood sample;
   b) adding the fluorochrome-coupled ligand to said sample;
   c) measuring a mean fluorescence intensity of the platelets ($MFI_{platelets}$) with a flow cytometer; and
   d) measuring a mean forward scatter (FSC) parameter with said flow cytometer and determining a $MFI_{platelets}/FSC$ ratio.

2. The process as claimed in claim 1, said blood sample is a sample of whole blood or a fraction of whole blood including platelets.

3. The process as claimed in claim 1, said ligand is an antibody or an antibody fragment.

4. The process as claimed in claim 1, said fluorochrome is a fluorochrome the excitation and emission wavelengths of which do not interfere with reagents for detecting RNA.

5. The process as claimed in claim 1, said $MFI_{platelets}$ measurement is normalized to the mean fluorescence intensity of an internal standard ($MFI_{standard}$) in order to obtain a normalized platelet mean fluorescence intensity ($MFI_{normalized\ platelets}$) and step c) consists in measuring the mean forward scatter (FSC) parameter with said flow cytometer to determine the $MFI_{normalized\ platelets}/FSC$ ratio.

6. The process as claimed in claim 5, said internal standard binds to said fluorochrome-coupled ligand.

7. The process as claimed in claim 1, the ligand binds at least partially to the MHC I alpha chain.

8. A process for identifying a population of platelets present in a blood sample, said process comprises the steps of:
   a) analyzing platelets present in a blood sample by carrying out the process as claimed in claim 1; and
   b) using the result of step a) to identify a population of platelets.

9. The process as claimed in claim 8, wherein the population of platelets is a population of young platelets.

10. A process for the in vitro diagnosis of peripheral or central thrombocytopenia in a subject comprising the steps of:
    a) analyzing platelets present in a blood sample of a subject by carrying out the process of claim 1; and
    b) using the result of step a) in the diagnosis of peripheral or central thrombocytopenia.

11. The process as claimed in claim 10, wherein a positive diagnosis for peripheral thrombocytopenia is given by an increase in said subject in the $MFI_{platelets}/FSC$ ratio and/or the $MFI_{normalized\ platelets}/FSC$ ratio relative to the same parameter(s) measured in a healthy subject.

12. The process as claimed in claim 10, wherein a positive diagnosis for central thrombocytopenia is given by parameter(s) $MFI_{platelets}/FSC$ ratio and/or $MFI_{normalized\ platelets}/FSC$ ratio in said subject similar or identical to the same parameter(s) measured in a healthy subject.

13. An in vitro process for prognosing the development of an inflammatory or cardiovascular disease, comprising the steps of:
    a) analyzing platelets present in a blood sample from a subject by carrying out the analysis process as claimed in claim 1;
    b) using the result of step a) in the prognosis of the development of inflammatory or cardiovascular disease.

14. An in vitro process for monitoring the therapeutic efficacy of a treatment for central or peripheral thrombocytopenia, comprising the steps of:
    a) analyzing platelets present in a blood sample of a patient having undergone central or peripheral thrombocytopenia treatment by carrying out the analysis process as claimed in claim 1;
    b) using the result of step a) in determining the therapeutic efficacy of the treatment of central or peripheral thrombocytopenia.

15. A kit for carrying out a process as claimed in claim 6, comprising:
    a ligand that binds to MHC I coupled to a fluorochrome;
    an internal standard; and
    instructions.

16. An in vitro process for prognosing the development of an inflammatory or cardiovascular disease, comprising the steps of:
- c) identifying a population of platelets present in a blood sample from a subject by carrying out the process as claimed in claim 8;
- d) using the result of step a) in the prognosis of the development of inflammatory or cardiovascular disease.

17. An in vitro process for monitoring the therapeutic efficacy of a treatment for central or peripheral thrombocytopenia, comprising the steps of:
- c) identifying a population of platelets present in a blood sample of a patient having undergone central or peripheral thrombocytopenia treatment by carrying out the analysis process as claimed in claim 8;
- d) using the result of step a) in determining the therapeutic efficacy of the treatment of central or peripheral thrombocytopenia.

18. The process as claimed in claim 3, wherein said antibody is a W6/32 antibody produced by a hybridoma ATCC HB-95 or a derivative which has retained its ability to bind MHC I.

19. The process as claimed in claim 6, wherein the internal standard is a polystyrene microbead that binds to the fluorochrome-coupled ligand.

20. A process for the in vitro diagnosis of peripheral or central thrombocytopenia in a subject comprising the steps of:
- a) identifying a population of platelets present in a blood sample of a subject by carrying out the process of claim 8; and
- b) using the result of step a) in the diagnosis of peripheral or central thrombocytopenia.

* * * * *